US011723535B2

(12) United States Patent
Vilser et al.

(10) Patent No.: US 11,723,535 B2
(45) Date of Patent: Aug. 15, 2023

(54) DEVICE AND METHOD FOR EXAMINING THE RETINAL VASCULAR ENDOTHELIAL FUNCTION

(71) Applicant: Imedos Systems GmbH, Jena (DE)

(72) Inventors: Walthard Vilser, Rudolstadt (DE); Jens Haueisen, Jena (DE); Sascha Klee, Erfurt (DE); Dietmar Link, Ilmenau (DE); Thomas Riemer, Jena (DE); Martin Skorsetz, Jena (DE)

(73) Assignee: IMEDOS SYSTEMS GMBH, Jena (DE)

( * ) Notice: Subject to any disclaimer, the term of this patent is extended or adjusted under 35 U.S.C. 154(b) by 0 days.

(21) Appl. No.: 17/553,764

(22) Filed: Dec. 16, 2021

(65) Prior Publication Data

US 2022/0160229 A1 May 26, 2022

Related U.S. Application Data

(62) Division of application No. 16/046,167, filed on Jul. 26, 2018, now Pat. No. 11,224,342.

(30) Foreign Application Priority Data

Mar. 29, 2018 (DE) ...................... 10 2018 107 625.8

(51) Int. Cl.
*A61B 3/12* (2006.01)
*A61B 3/14* (2006.01)
*A61B 3/00* (2006.01)

(52) U.S. Cl.
CPC .............. *A61B 3/12* (2013.01); *A61B 3/0008* (2013.01); *A61B 3/14* (2013.01); *A61B 3/1241* (2013.01)

(58) Field of Classification Search
CPC ........... A61B 3/12; A61B 3/0008; A61B 3/14; A61B 3/1241
(Continued)

(56) References Cited

U.S. PATENT DOCUMENTS

| 6,621,917 B1 | 9/2003 | Vilser |
| 2007/0030450 A1 | 2/2007 | Liang et al. |
| 2007/0276260 A1* | 11/2007 | Hammer ............ A61B 5/02007 |
| | | 600/479 |

FOREIGN PATENT DOCUMENTS

| WO | 99/29229 A1 | 6/1999 |
| WO | 00/71019 A1 | 11/2000 |

(Continued)

OTHER PUBLICATIONS

Garhofer, G et al., Use of the retinal vessel analyzer in ocular blood flow research, Acta Ophthalmologica, 2010, pp. 717-722, v. 88.
(Continued)

*Primary Examiner* — Marin Pichler
*Assistant Examiner* — Mitchell T Oestreich
(74) *Attorney, Agent, or Firm* — Patentbar International (57) ABSTRACT

The invention relates to a device and a method for examining the retinal vascular endothelial function of the vessels of the retina at the fundus (F) of a patient's eye. Using a fundus camera, the vessels of the retina are stimulated with flicker light during a stimulation phase and sequences of images of areas of the fundus (F) are recorded, from which vascular parameters are derived which describe the retinal vascular endothelial function of the vessels. By imaging a macula stop (MB), which covers the macula, onto the fundus (F), the fundus (F) can be illuminated with a higher light intensity, which improves the stimulation effect and the image quality and/or reduces the strain on the patient.

7 Claims, 9 Drawing Sheets

(58) Field of Classification Search
USPC .......................................................... 351/206
See application file for complete search history.

(56) References Cited

FOREIGN PATENT DOCUMENTS

| | | |
|---|---|---|
| WO | 2005/094668 A1 | 10/2005 |
| WO | 2013/120085 A2 | 8/2013 |

OTHER PUBLICATIONS

Vilser, W et al., Quantitative assessment of optic nerve head pallor, Physiological Measurement, 2008, pp. 451-457, v. 29, IOP Publishing.

O'Brien et al., Imaging system to assess objectively the optical density of the macular pigment in vivo, Applied Optics, Sep. 1, 2013, pp. 6201-6212, vol. 52, No. 25.

\* cited by examiner

DEVICE AND METHOD FOR EXAMINING THE RETINAL VASCULAR ENDOTHELIAL FUNCTION

RELATED APPLICATIONS

This application is a Divisional of U.S. application U.S. Ser. No. 16/046,167, filed on Jul. 26, 2018, which, in turn, claims priority to German Patent Application DE 10 2018 107 625.8, filed Mar. 29, 2018, both of which are incorporated herein by reference in their entirety.

FIELD OF THE INVENTION

The area of application of the invention relates to the entire field of vascular medicine, e.g. ophthalmology, neurology, cardiology, nephrology, diabetology, and hypertensiology.

BACKGROUND OF THE INVENTION

It is known from studies that microvascular changes are frequently of a systemic nature, i.e. they occur similarly in the vessels, in particular the microcirculation vessels of all organs in the human and animal body, and, depending on the organ, lead to different manifestations of cardiovascular conditions, such as atherosclerosis, arteriosclerosis, cardiac insufficiency, renal insufficiency, eye conditions, e.g. retinopathies and glaucoma, cerebrovascular conditions, e.g. vascular dementia, and may ultimately trigger or are predictors of cardiovascular events, such as myocardial infarction and stroke.

As a unique optical window to microcirculation, the eye allows the retinal vessels to be examined as a mirror image of the vessels and their functions in inaccessible regions of the other organs in the body. A preferred area of application of the invention consists in supplementing vascular diagnostics of the large vessels with the vascular diagnostics of microcirculation and, in particular, the function diagnostics of the vascular endothelial function or vascular dysregulation, respectively.

In ophthalmology, imaging techniques are currently used, above all, in clinical examinations of structural or morphological changes in the eye, in particular in the ocular fundus (in the retina). This includes conventional fundus cameras, OCTs and laser scanners. Vascular examination by means of static vessel analysis, e.g. using the VesselMap available from Imedos, has begun to penetrate everyday clinical practice in microvascular risk stratification and therapy monitoring.

So far, functional examination of the retinal vessels has been applied only in research, e.g. devices and methods for measuring blood velocity and vessel diameters on the basis of indicators, based on Doppler or OCT measurements as well as systems for dynamic vessel analysis. The areas of application of Doppler- or OCT-based systems provide statements which have hardly achieved any significance outside ophthalmology and do not enable function diagnostics of autoregulation or of the endothelial function, respectively.

Dynamic vessel analysis enables the examination of various autoregulation mechanisms on the basis of continuous measurements of the vessel diameters over time and along the location of the large arteries and veins of microcirculation. The retinal vessels and microcirculation, respectively, are stimulated or provoked during the measurement and recording of the vessel diameters and respond accordingly by constriction or dilation, which describes the vessel response of the retinal autoregulation addressed by the respective type of stimulation or provocation and its functionality.

Such stimulation or provocation methods allow examination of various autoregulation mechanisms of microcirculation. One of said autoregulation mechanisms is flow-induced autoregulation. In this case, stimulation is effected by flicker light (rhythmic interruption of the flicker light at a defined frequency), but owing to the technological shortcomings of the measuring light being simultaneously used as the flicker light, the parameters for the measuring light and the flicker light are not independently adjustable.

The dynamic vessel analysis system constituting the prior art is the Retinal Vessel Analyzer (RVA) or Dynamic Vessel Analyzer (DVA), respectively, from Imedos (Garhofer, G., Bek, T., Böhm, A. G., Gherghel, D., Grunwald, J., Jeppesen, P., Kergoat, H., Kotliar, K., Lanzl, I., Lovasik, J. V., Nagel, E., Vilser, W., Orgul, S., Schmetterer, L.: "Use of the retinal vessel analyzer in ocular blood flow research". Acta Ophthalmologica 2010: 88: pages 717-722.) The standard provocation used in the RVA/DVA is flicker light operating at a frequency of 12.5 Hz. White halogen lamp light in the continuous illumination beam path of a conventional fundus camera is spectrally modified to green measuring light by a bandpass filter and is rhythmically interrupted by an electro-optical shutter during the fixed stimulation phases of usually 20 s. The examination consists of 3 phases, the first phase (baseline phase BP) recording the baseline vessel diameter and being used as a reference for computing vessel responses on a percentage basis. The second phase is the stimulation phase (SP), in which the vessel response to flicker light is recorded. The third phase will be referred to as the posterior phase (NP) because in this phase, the vessel diameter returns to baseline. The second and third phases are repeated alternately three times and the vessel responses are then superimposed upon each other for averaging and evaluated with respect to the maximum dilation (maximum flicker dilation $FD_{max}$) and subsequent constriction.

In the prior art these measurements, obtained by the aforementioned DVA, are restricted to the large vessels of microcirculation between 60 and 300 µm.

The evaluated parameters of the vessels, such as the maximum flicker dilation $FD_{max}$, as well as other derivable parameters, are interpreted as biomarkers for the function diagnostics examination of the microvascular endothelial function. Erroneously, some authors also refer to and interpret the parameters of the vessel response as parameters of neurovascular coupling NVC. However, there is evidence that, while neurovascular coupling NVC may represent the initial stimulus, the $FD_{max}$ of the vessel response of the large vessels describes the function of the vascular endothelial cells, thus characterizing the vascular endothelial function, and that the vascular endothelial function or endothelial dysfunction or vascular dysregulation, respectively, can be examined.

The examination technology of the aforementioned DVA is too rigid, and allows neither any extension of the medical examinations by changing the type and form of light stimulation nor any optimization for sufficiently stable and high dilation responses. Moreover, the inflexible illumination causes high production costs, additional scattered light and reflection light, in particular on the vessels, thereby reducing the accuracy and reliability of the medical statement as well as the range of applications in research and clinical practice. The production cost is high, the examination puts a strain on the patient and the reproducibility of the parameters of the vessels for individual examination is still not sufficiently satisfactory. The aforementioned DVA uses a monochromatic digital image sensor and only one spectral wavelength range in green light, which also generates measuring light and stimulation light. Owing to its principle, the electro-optical shutter causes a dependence of the modulation on measurement and stimulation light, as a result of which the arrangement can be optimized either only for measurement or only for stimulation. However, the optimization criteria differ greatly between both types of illumination. Furthermore, subjective errors caused by the examiner occur and the examination places high demands on the examiner in handling the patient and the aforementioned DVA. Moreover, the inflexible and rigid technical solution of generating the stimulation light by the DVA yields only a limited range of applications of the DVA in function diagnostics using flicker light in research and clinical practice.

Further, WO 2005/094668 A1 describes a device for photometrically measuring the vessel diameters of smaller vessels. The disclosed technical solution allows the measurement of vessel diameters in the area of the arterioles and venules, provided the vessels in the fundus image are selectable as vessels. For this purpose, two different spectral wavelength ranges of a color camera are used. This considerably increases the retina's exposure to light. However, another substantial disadvantage of the disclosed solutions also consists in the fixed illumination-side arrangement of a light modulator in the joint illumination-side beam path of both color channels of the color camera, which likewise only allows flexible temporal modulation and substantially restricts the range of applications and adaptivity. Ultimately, the device of the aforementioned WO 2005/094668 A1 has the same disadvantages as the aforementioned DVA, except for the advantage that measurements can be performed even on small retinal vessels, which are significantly larger than capillaries, however.

Another technical solution for measuring capillary "perfusion" is described in the article by Vilser et. al. from 2008 (Vilser, W., Nagel, E., Seifert, B. U., Riemer, T., Weisensee, J., Hammer, M: "Quantitative assessment of optic nerve head pallor". Physiological Measurement 29 (2008), pages 451-457). Using a dual bandpass filter in the illumination beam path of a conventional fundus camera, two spectral regions in the red and green spectral ranges of the white illumination light are selected and assigned to a red color channel and a green color channel of a 3-chip color image sensor such that both selected illumination-side wavelengths are received separately by the two assigned red and green color channels of the color image sensor. Based on the color intensities detected by the pixels of both color channels (red and green), each of which color intensities can be assigned to the same fundus point, quotients are formed and in turn assigned to the fundus location. The resulting quotient image is then evaluated with respect to the capillary perfusion on the optic nerve head.

Although this method does not allow representation of the perfusion of the optic nerve head, if perfusion is understood to mean the capillary blood flow, but it provides a measure of the blood volume and, thus, of the capillary vessel diameter and the capillarization of the examined tissue volumes. The disadvantage of this method is that, in contrast to the description in the aforementioned article, it cannot provide functional statements about the regulation of capillary perfusion.

SUMMARY OF THE INVENTION

It is the object of the invention to find a method by which an examination of the retinal vascular endothelial function puts less of a strain on the patient.

It is also the object of the invention to find a device suitable to carry out the method.

An essential technical feature of a device according to the invention is that a macula stop is arranged in its illumination beam path, in a plane conjugated to the fundus.

The prior art assumes that the flicker stimulation in the area of the macula is decisive for the dilation of the large vessels of the retina. According to the invention, however, it is exactly the area of the macula which is covered by a macula stop on the illumination side and is, thus, not stimulated by flicker light, which surprisingly does not affect the response of the large vessels (vessel response) that are exposed to measurement and flicker light outside the macula.

The following advantages result from the use of the macula stop:

It drastically reduces the patient's exposure to light, because the light-sensitive macula remains covered during the examination.

Alternatively, more light can be used in the stimulation and measurement area not covered by the macula stop, i.e. in the light field on the fundus not covered by the macula stop, so that the fundus outside the macula can be illuminated with a higher light intensity, which results in an improved signal-to-noise ratio, enhances the stimulation effect, increases dilation and significantly improves the image quality in the measurement area around the macula stop.

With the macula shaded by the macula stop, the high brightness contrast makes it easier for the patient to find and focus on a fixation mark provided for internal fixation of the foveola. Restless eye movements interfering with the examination are significantly reduced, which considerably improves the quality of the measurements.

Another advantage is that by centrally arranging the macula stop, reflections on the ophthalmoscope lens of the fundus camera can be blocked out completely. This also considerably reduces scattered light affecting the image, especially scattered light from the central area of the superimposed illumination-side and image-side beams, which appears as irritating, contrast-reducing brightening in the image of the fundus.

Accordingly, complex and expensive optical units connected with anti-reflection measures can be dispensed with in the illumination beam path of the fundus camera. The overall length and the cost of developing and manufacturing the fundus camera can be comparatively reduced. Furthermore, the luminous flux into the eye is reduced.

The macula stop and optionally, according to the invention, further stops inserted in the illumination beam path provide field areas, within the light field, for the use of further beam paths or beams, which serve the purpose of exact, automatable adjustment of the fundus camera to the eye and, thus, of eliminating sources of errors and are advantageously usable directly with the digital image sensor of the fundus camera, without additional detectors.

Advantageously, there is a partly transparent web on the macula stop. The web serves, on the one hand, as a mechanical holder for the macula stop and, on the other hand, as another stop inserted in the illumination beam path in order to cover the optic nerve head (papilla), so as to optimize the dynamic range of the digital image sensor of the fundus camera and avoid overexposure by very bright surface areas of the optic nerve head.

Advantageously, the illumination unit of the fundus camera is an adaptive, geometrically structurable illumination unit, e.g. in the form of an annular LED array. This allows the flicker light and the measuring light to be generated independently of each other, be it temporally, geometrically, spectrally or with respect to temporal intensity control.

In a device for examination of the retinal vascular endothelial function of the vessels of the retina at the fundus of an eye, said device comprising a fundus camera with an observation beam path including a digital image sensor designed to record image sequences of areas of the fundus, onto which the observation beam path of the fundus camera focuses, and with an illumination beam path in which an illumination unit is arranged in a plane conjugated to the pupil of the eye, for illumination of the fundus with a measuring light and a flicker light within a light field on the fundus that is limited by the image of a field stop, which is arranged in a plane conjugated to the fundus in the illumination beam path, the object of the invention is achieved in that at least one macula stop is arranged in the plane conjugated to the fundus in the illumination beam path, said stop being provided with a respective fixation mark, so that one of the at least one macula stop covers the macula on the fundus when the eye fixates on the fixation mark of the one macula stop.

The macula stop is advantageously a mechanical stop or an optoelectronic stop, e.g. a transmission display.

Advantageously, exactly one macula stop is present, which is arranged in the plane conjugated to the fundus in the illumination beam path, and the fixation mark is a punctiform opening in an area center of the macula stop.

Further, a partly transparent web preferably abuts the macula stop, said web being radially aligned to the area center of the macula stop and by which web the papilla at the fundus can be covered, so that the radiation intensity of an image of the papilla can be adapted to a dynamic range of the digital image sensor that is designed for the radiation intensity of an image of the areas of the fundus surrounding the papilla.

Advantageously, another partly transparent stop, adjustable in transparency, is present to cover the papilla.

The macula stop is preferably movable in the plane conjugated to the fundus in the illumination beam path, with the area center of the macula stop remaining located within the field stop, so that different selected areas of the fundus are illuminated by the light field and sequences of images of the different selected areas of the fundus can be recorded.

Preferably, exactly one macula stop is formed on the field stop such that the fixation mark is located within the field stop in a manner abutting an inner edge, and the field stop is rotatable about an optical axis of the illumination beam path, so that different selected areas of the fundus are illuminated by the light field and sequences of images of the different selected areas of the fundus can be recorded.

Another preferred variant consists in that exactly four macula stops are formed in diagonally opposite pairs on the field stop such that the respective fixation mark is located within the field stop in a manner abutting an inner edge, so that different predetermined areas of the fundus are illuminated by the light field and, alternatively, sequences of images of the different predetermined areas of the fundus can be recorded.

Advantageously, the illumination unit is formed by an adaptive, structurable arrangement of light sources, in the plane conjugated to the pupil, which can be switched on and off and/or modulated in their intensity, regardless of location, spectrum and time and separately. This makes it possible to implement a great diversity of illumination structures. When selecting and controlling individual light sources, the respective active (light-emitting) light sources define the geometry, e.g. a ring, a half ring, or ring segments, and the dimension of the illumination structure, e.g. by an internal diameter $d_i$ and an external diameter $d_a$. By driving spectrally different light sources, illumination structures differing in time and space can be formed for different spectral ranges. An illumination unit designed in this manner is an advantageous embodiment of a device according to the invention. However, a device according to the prior art equipped with an illumination unit according to the invention will also achieve the object of the invention by itself, without a macula stop.

Preferably, an image of the field stop arranged in the illumination beam path has a smaller cross-section on the digital image sensor than a reception surface of the digital image sensor, and the brightness distribution in a resulting differential area is used to determine a scattered light distribution by which the images of the image sequences can be corrected.

In a method for examination of the retinal vascular endothelial function of the vessels of the retina at the fundus of an eye, said method comprising the process steps of adjusting a fundus camera to the eye, generating measuring light for illumination of the vessels of the retina at the fundus and of flicker light for stimulation of the vessels of the retina at the fundus during a stimulation phase, generating a sequence of images of an area of the fundus during a baseline phase, at least one stimulation phase and at least one posterior phase, measuring the vessel diameter of selected vascular segments of the vessels of the retina in the images of the generated image sequence as a function of location and time, performing movement correction of the measured vascular segments, wherein each movement-corrected vascular segment is assigned to a location on the fundus, forming diameter signals, which respectively represent the measured vessel diameters as a function of the time and location of the respectively selected vascular segment, and deriving vascular parameters from the diameter signals, each of said parameters describing the endothelial function of the respectively selected vascular segment, the object is further achieved either in that the illumination and stimulation of the macula at the fundus is prevented by sharply imaging on the fundus at least one macula stop, on which a fixation mark is located, and the eye being aligned with said one macula stop by fixation on the fixation mark of one of said at least one macula stops such that the macula is covered by an image of said one macula stop, or in that the fundus is illuminated by an adaptively structurable arrangement of light sources, which can be adapted to the respective opening of the pupil and to other given conditions by a generated illumination structure and by which the measuring light and flicker light can be adjusted independently of each other.

Advantageously, sequences of images of different selected areas of the fundus are recorded sequentially, in each case after exactly one macula stop imaged onto the fundus has been shifted to a different location, so that its image on the fundus has been shifted and the eye, fixating on the fixation mark, has followed.

Further advantageously, the location parameters of the locations of the macula stop are stored and are retrievable and adjustable again for repeat and follow-up measurements.

Alternatively, image sequences of different predetermined areas of the fundus are preferably recorded, while four macula stops, which are arranged diagonally opposite each other, are imaged onto the fundus and the eye has sequentially fixated on a different one of the fixation marks in each case.

The durations of the baseline phase, the stimulation phase and the posterior phase and the parameters of the measuring light and of the flicker light are preferably adjusted independently and are stored, in a manner assigned to a patient and to an examination program, so as to be retrievable and adjustable again as a set of parameters for repeat and comparative examinations.

The maximum flicker dilation is advantageously determined as one of the derived vascular parameters and is output in a measurement report together with a graphical representation of averaged diameter signals that are each respectively generated for the selected arterial and venous vascular segments on the basis of the diameter signals formed for this purpose.

Advantageously, the maximum flicker dilation is assigned, in a color-coded manner, to the respective vascular segment in a mapping image for functional imaging of the endothelial function, wherein a missing vasodilation or a vasodilation below a predetermined threshold value is marked in red and a vasodilation above a threshold value, which corresponds to a healthy vascular function, is marked in green on the associated vascular segment, and the mapping image is output as a graphical examination result.

BRIEF DESCRIPTION OF THE DRAWINGS

The invention will be explained in more detail with reference to the following exemplary embodiments with the help of drawings, wherein.

DETAILED DESCRIPTION OF THE PREFERRED EMBODIMENTS

Figure 1:
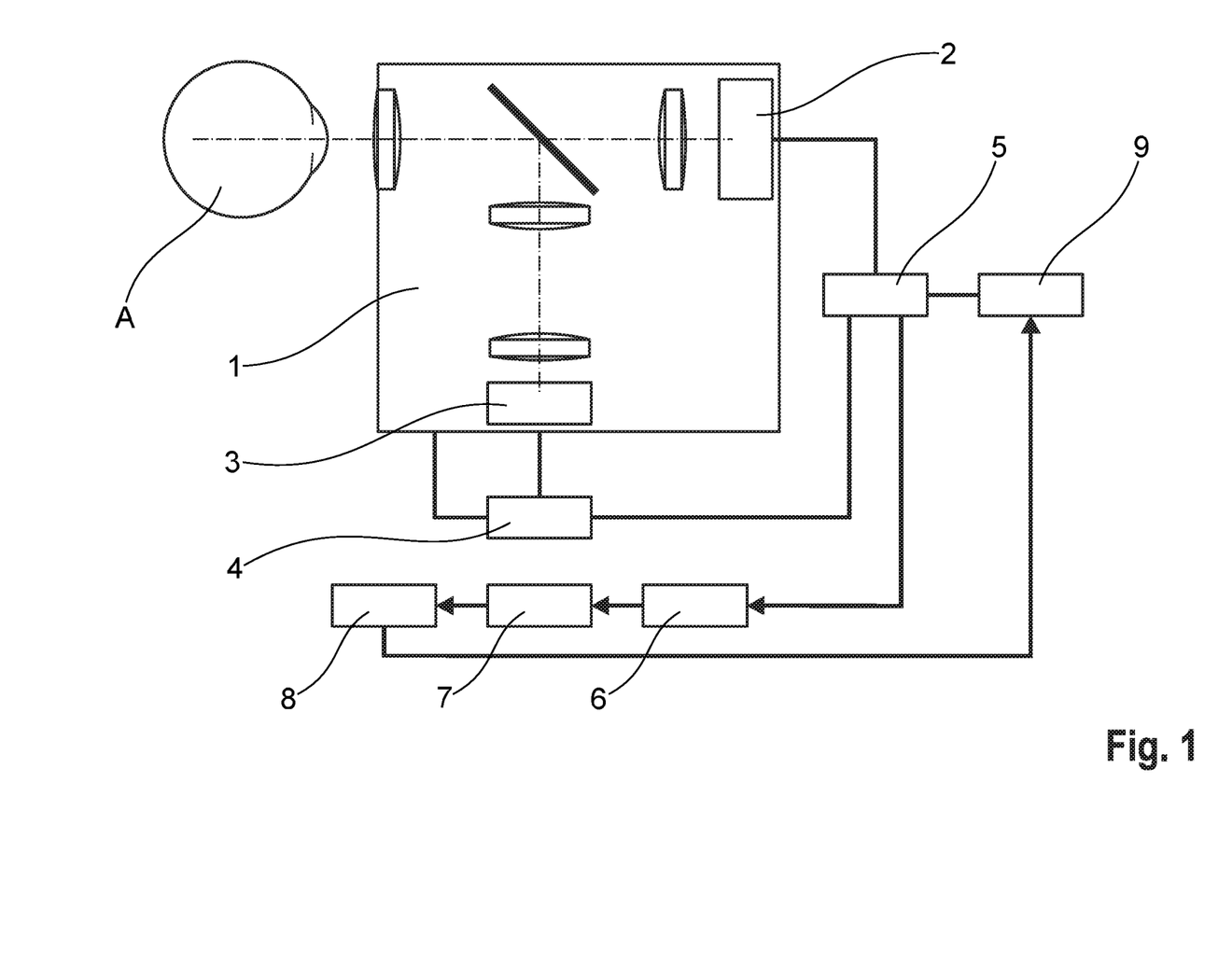
FIG. 1 shows a block diagram of a device according to the invention.

An embodiment of a device according to the invention is shown as a block diagram in FIG. 1. Similar to a device known from the prior art, the device according to the invention comprises a fundus camera 1 with a digital image sensor 2 and an illumination unit 3, a control unit 4, a data and image processing unit 5, a unit for generating diameter signals 6, a signal analysis unit 7, a result and presentation unit 8 and an input and output unit 9. The device differs from a prior art device of the same generic type essentially in the design of the fundus camera 1 and advantageously in the design of the illumination unit 3.

Figure 2:
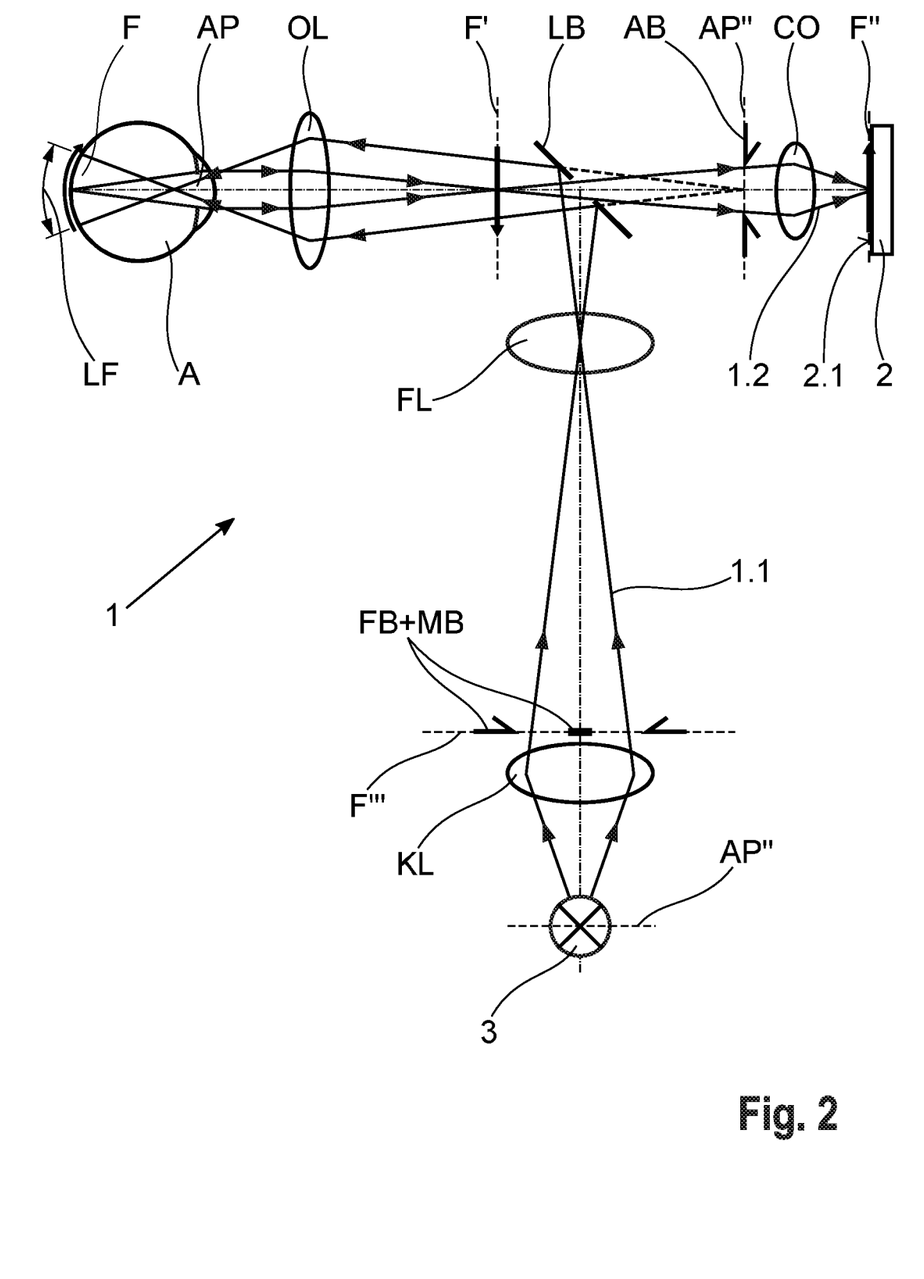
FIG. 2 shows an optics diagram of a fundus camera according to the invention.

FIG. 2 shows an optics diagram of a fundus camera 1. The latter includes an illumination beam path 1.1 and an observation beam path 1.2 (imaging beam path).

In the simplest case, the observation beam path 1.2 has two lenses, namely an ophthalmoscope lens OL and an objective lens CO, via which the fundus F of the eye A, on which the fundus camera 1 has been focused, is imaged into a plane F''', which is conjugated to the fundus F and located on a reception surface 2.1 of the digital image sensor 2.

The illumination beam path 1.1 is coupled into the observation beam path 1.2 by a pinhole stop LB and, in the simplest case, includes a collimator lens KL and a field lens FL. The illumination unit 3 is arranged in a plane which is conjugated to the pupil AP and located in the illumination beam path 1.1 and is imaged into the pupil AP. The field stop FB, which is arranged in a plane F'' conjugated to the fundus F in the illumination beam path 1.1, is imaged sharply on the fundus F and on the reception surface 2.1 of the digital image sensor 2.

It is essential to the invention that a macula stop MB is present, in addition, in the illumination beam path 1.1. The macula stop MB is preferably arranged in a same plane as the field stop FB, but both may also be arranged in different planes conjugated to one another. In this case, the macula stop MB may be arranged in a fixed or movable manner within the field stop FB, which is typically formed by a ring. Various advantageous embodiments will be explained with reference to exemplary embodiments.

Figure 4A:
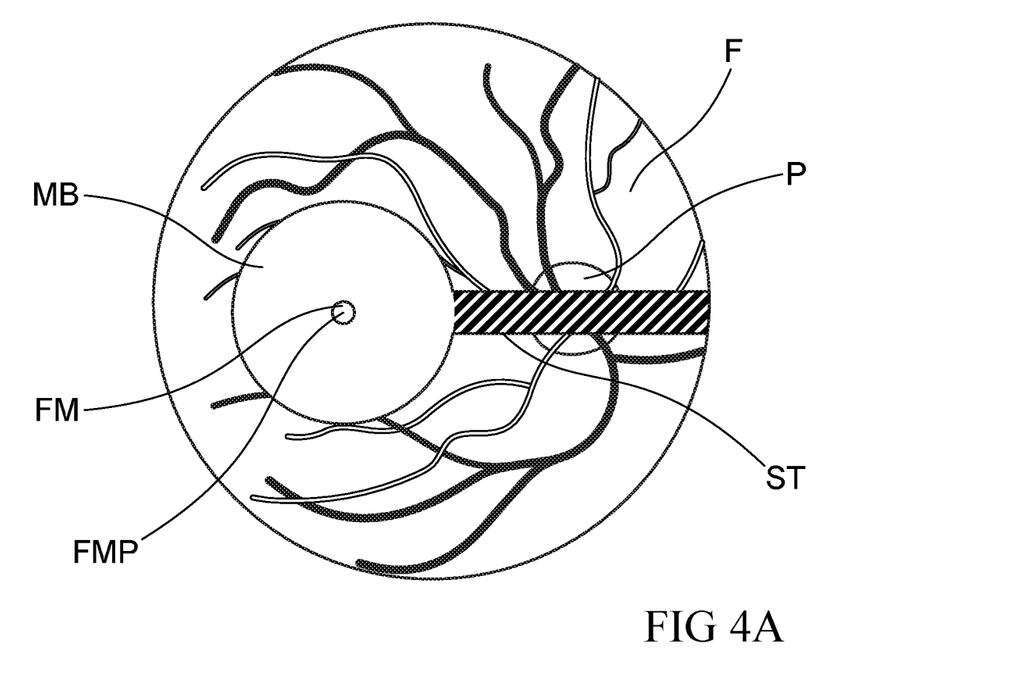
FIG. 4A shows a macula stop imaged centrally on the fundus.

According to a first exemplary embodiment shown in FIG. 4A, the macula stop MB is circular, arranged centrally, i.e. its area center FMP is located on the optical axis of the illumination beam path 1.1, and is imaged onto the fundus F at a field angle of 15°. For internal fixation, the macula stop MB has a small opening as a fixation mark FM around its area center FMP. As an alternative, instead of using the opening as a fixation mark FM, small light sources, e.g. LEDs, structured as points, rings or crosses, may be reflected as luminous fixation marks FM in temporally, geometrically and spectrally different manners, controllable via the control unit 4. On the one hand, this allows different adjustments to be made of the fundus F with respect to the macula stop MB, due to said geometric structuring. On the other hand, flashing fixation marks FM or color changes may increase the patient's attention or may be adapted to the visual capacity of the patient's eye. The eye A to be examined may also be fixed by external fixation, so that no fixation mark FM is required within the fundus camera 1. In particular, if the visual capacity of the eye A to be examined is so low that it cannot fixate on a fixation mark FM, it makes sense to provide to the eye A not to be examined a fixation mark FM which is located outside the fundus camera 1 and is positioned to match the location of the macula stop MB.

Figure 4B:
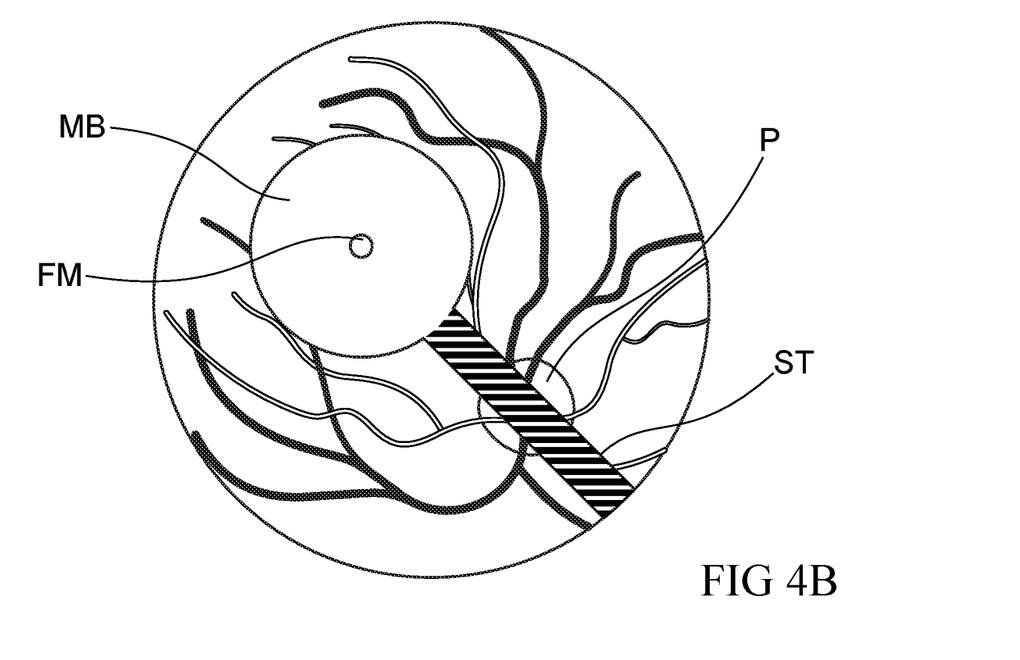
FIG. 4B shows a macula stop imaged eccentrically on the fundus.

FIG. 4B shows the macula stop MB in a position shifted with respect to FIG. 4A. Accordingly, a different area of the fundus F is now located within the light field LF, which is limited by the image of the field stop FB on the fundus F.

Figure 3:
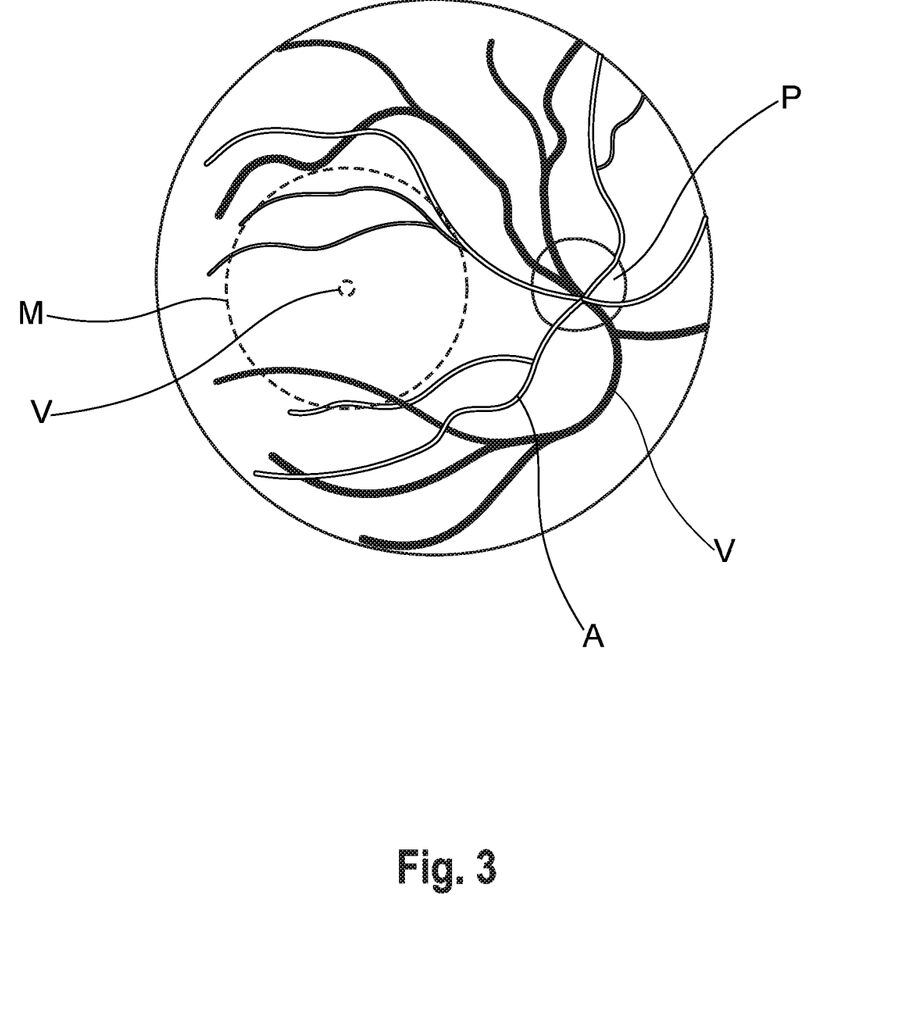
FIG. 3 shows an area (light field) of the fundus of an eye illuminated in a manner limited by the image of a field stop.

FIG. 3 schematically shows a structure of the fundus F of an eye A for easy understanding. It also shows, in addition to large arteries $A_V$ (light gray) and large veins $V_V$ (dark gray): the macula M, the area with the highest density of photoreceptors (yellow spot) and, thus, the most light-sensitive area of the fundus F, the foveola V, the fovea centralis at the center of the macula M, by which the eye A fixates on a fixation mark FM, and the papilla P (optic nerve head, blind spot), the exit point of the optic nerve from the envelope of the eyeball, which is supplied with relatively little blood.

The field stop FB and the macula stop MB are axially movable together in the illumination beam path 1.1, allowing the macula stop MB to be imaged onto the fundus F so as to be sharply visible for the patient.

Advantageously, a web ST is present, which is radially aligned with the area center FMP, said web ST serving as a mechanical holder for the macula stop MB and being rotatable by 180° against the light field center when changing the eye A to be examined from the right eye A to the left eye A.

In an advantageous alternative embodiment, the web ST may be so wide and transparent that it covers the papilla P in order for the intensity of the measuring light reflected in the area of the papilla P to be adjusted to the surrounding retina and, thus, to the dynamic range of the digital image sensor 2.

In an advantageous design of the exemplary embodiment for further medical examinations, means are provided which allow the macula stop MB to be moved radially in the light field LF. Due to the fact that, by following the fixation mark FM, the eye A to be examined follows the macula stop MB such that the macula M is always covered by the macula stop MB, the papilla P and individual selected retinal vessel trees are arranged more centrally in the light field LF for measurements and can be examined.

Another advantageous embodiment is the stationary arrangement of one or more macula stop MB on the inner edge of the field stop FB. The advantage of such an embodiment is the fast, easy adjustment of the fundus F or of the measuring points, respectively, in a manner which is standardized for different eyes and which is reproducible for repeat measurements.

Figure 5A:
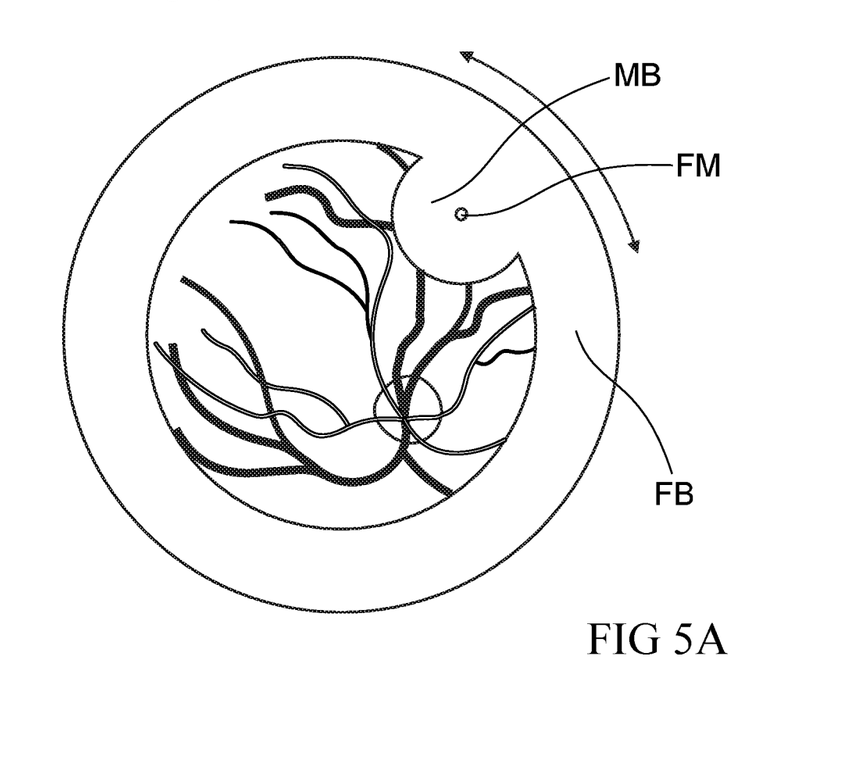
FIG. 5A shows a macula stop formed on the field stop and imaged on the fundus.

FIG. 5A shows an embodiment in which a macula stop MB is firmly connected to or designed monolithically with the field stop FB. By rotating the field stop FB about its center, which is located on the optical axis of the illumination beam path 1.1, the eye A is maximally deflected in a circulatory movement, allowing a maximum overall area of the fundus F to be sequentially illuminated, imaged and, consequently, examined.

Figure 5B:
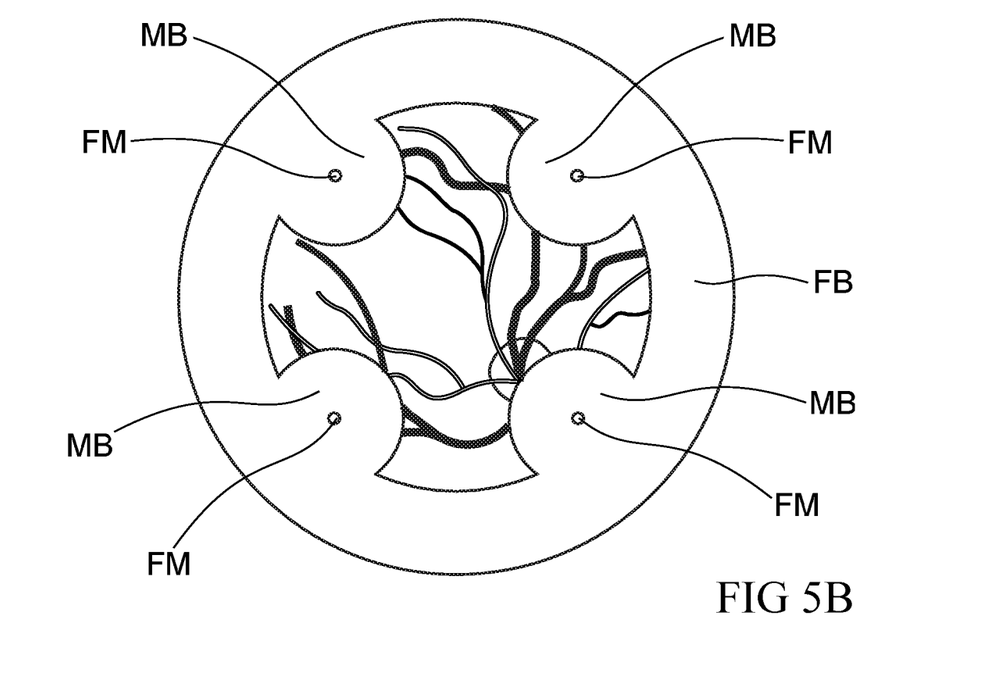
FIG. 5B shows four macula stops formed on the field stop and imaged on the fundus.

FIG. 5B shows an embodiment in which four macula stop MB are formed on the inner edge of the field stop FB in opposite pairs or offset by 90° with respect to each other, respectively. For this case, it is envisaged for the patient's eye A to fixate sequentially on at least the fixation marks FM of two opposite macula stops MB, by which predetermined areas of the fundus F are illuminated and imaged.

The data and image processing unit 5 is preferably configured such that the image of the macula stop MB, optionally with the web ST, in the image provided to the examiner is cleanly blocked out electronically by software.

Figure 6:
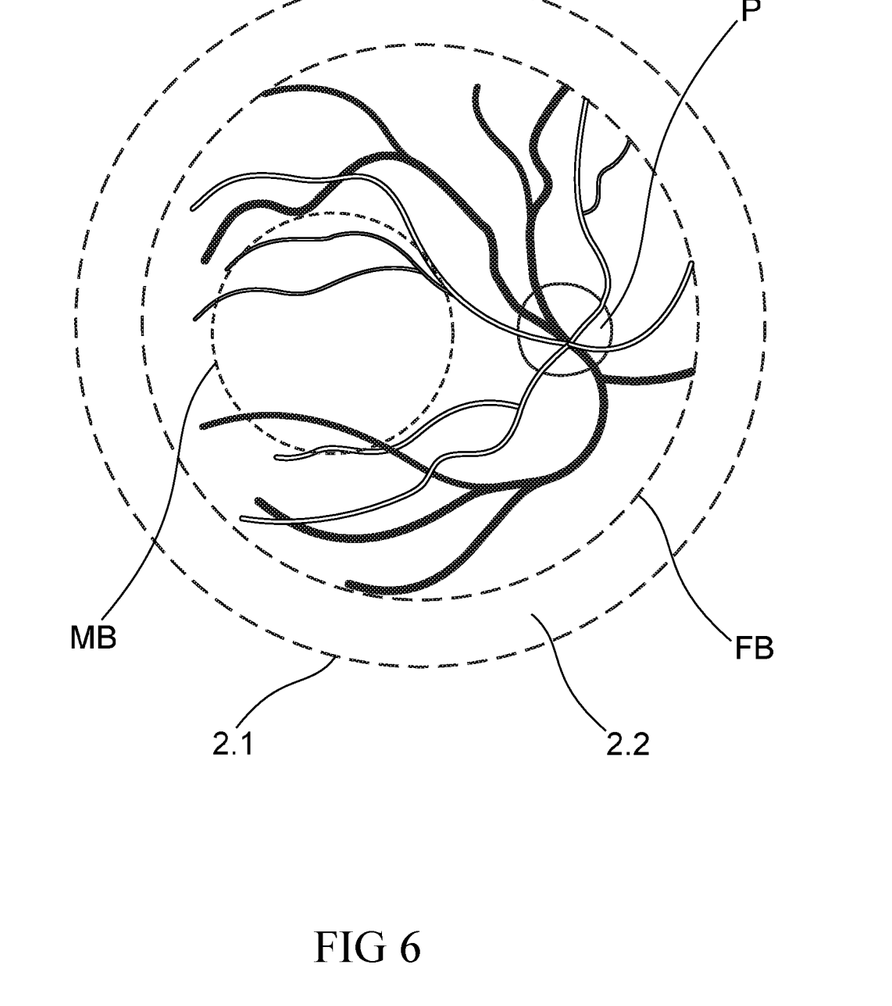
FIG. 6 shows the images of the field stop as well as of the macula stop on the reception surface of the digital image sensor.

The field stop FB, which limits a light field LF on the fundus F, is preferably imaged on the reception surface 2.1 of the digital image sensor 2 with a smaller cross-section than the cross-section of the reception surface 2.1. In contrast to the prior art, where the size of the image of the field stop FB is regularly adapted to the size of the reception surface 2.1 of the digital image sensor 2 and, thus, the reception surface 2.1 is fully illuminated, this generates a differential area 2.2 outside the image of the fundus F, which can be used to compute the scattered light distribution as well as to monitor the non-reflecting and low-scatter adjustment of the fundus camera 1 to the eye A. In this case, it does not matter whether parts of the differential area 2.2 are made accessible to the examiner as adjustment aids or are used for automatic adjustment processes. The data and image processing unit 5 determines the brightness distribution on the reception surface 2.1 of the digital image sensor 2 within the image of the macula stop MB and in the differential area 2.2, thereby computing the scattered light distribution in the image of the fundus F on the digital image sensor 2 via an approximation algorithm and correcting the image accordingly.

The illumination beam path 1.1 further includes, as the illumination unit 3 according to the invention, a preferably adaptively structurable circular or annular arrangement of small light sources, e.g. three groups of LEDs with different spectral properties, preferably in the blue, green and red spectral ranges, said groups of LEDs being arranged in the illumination beam path 1.1 in a plane AP''' conjugated to the plane of the pupil AP. By differentiated control of the LEDs, the respectively controlled (active) LEDs form an adaptive illumination structure.

Said LEDs are controlled via the adaptive control unit 4 such that the LED light intensities of the different-colour LEDs are modeled separately and independently of each other. The modulation of the LED light is intended to enable both the adjustment of the intensity of continuous light as measuring light and the adjustment of stimulation light alternating between high and low intensity, with adjustable parameters of the frequency, the modulation depth and the alternating light shape (e.g. wave-shaped to step-shaped, symmetrical or asymmetrical change between bright and dark phases). Also, the illumination structure, which is respectively determined by the temporally controlled (active) LEDs of a group or of a spectral range, respectively, can be adjusted to the requirements for different examinations. For instance, the illumination structure may be formed by the temporally and locally controlled active LEDs as temporally changing narrower or wider rings, half rings, ring segments or points, which can be used to reduce scattered light and reflection light and to adapt the opening of the pupil AP.

The opening of the pupil may differ individually to a great extent, depending on whether the examination is performed in the non-mydriatic or mydriatic mode, also depending on the light conditions and on the patient. In order to reduce the patient's exposure to light and to provide optimal conditions for imaging and measurement, an external diameter $d_a$ of the illumination structure is adapted to the opening of the pupil AP. An internal diameter $d_i$ of the illumination structure is adapted to the size of the image AB' of an aperture stop AB arranged in the observation beam path 1.2 in a plane AP''' conjugated to the pupil AP. Advantageously, the internal diameter $d_i$ of the illumination structure is greater than the diameter of the image AB' of the aperture stop AB. Adapting this radiation-free space between the illumination light and the imaging light allows the influence of reflections or scattered light to be reduced as a function of the individual conditions of the patient's eye.

Also, a structural change rotating during the examination or differentiated local control of the LEDs, respectively, may be used to capture image sequences with different illumination structures, allowing the angle at which the illumination radiation is incident on a fundus object (e.g. vessels) to be varied such that vascular reflections are reduced and local image contrasts are increased.

The adaptive adjustment, in particular of the external diameter $d_a$ of the illumination structure, also allows the dynamic vessel analysis in the mydiatric mode to be switched very quickly to the mode of non-mydriatic static vessel analysis, and vice versa. At the same time, said adaptivity also allows the fundus F to be focused via the principle of Scheiner apertures.

FIGS. 7A to 7E show examples of different embodiments of the illumination unit 3 as an adaptive, structurable arrangement of light sources.

Each of said figures shows an image of the illumination unit 3 in the plane of the pupil AP together with an image AB' of the aperture stop AB arranged in the observation beam path 1.2. The illumination unit 3 advantageously represents a circular or annular arrangement of LEDs in a ring shape.

Figure 7A:
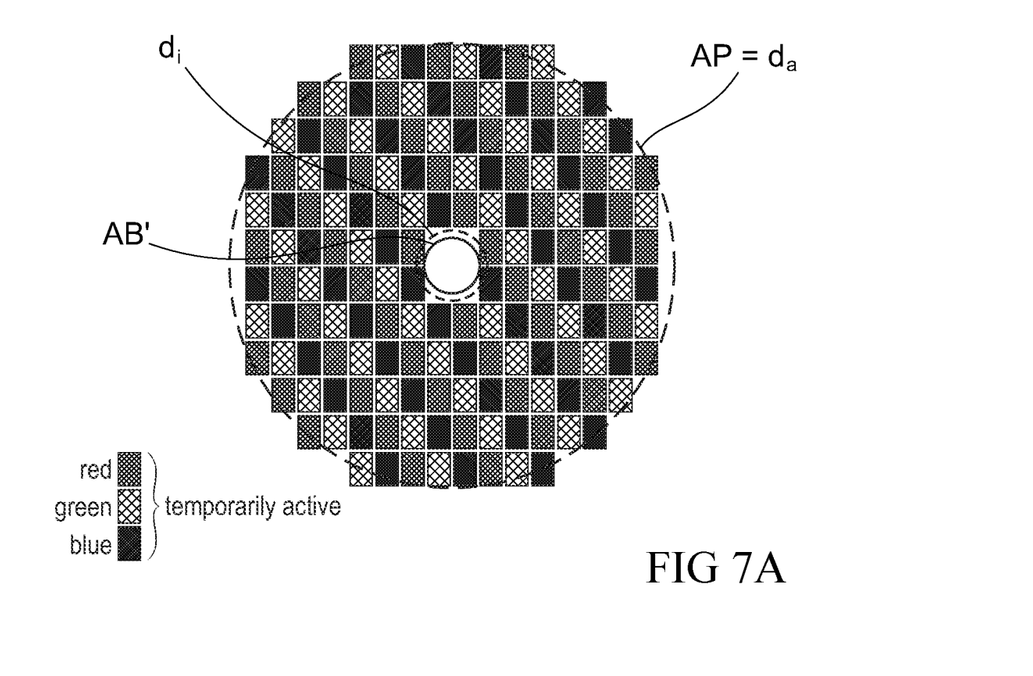
FIG. 7A shows a first embodiment example of an illumination unit as an adaptive, structurable arrangement of light sources.
Figure 7B:
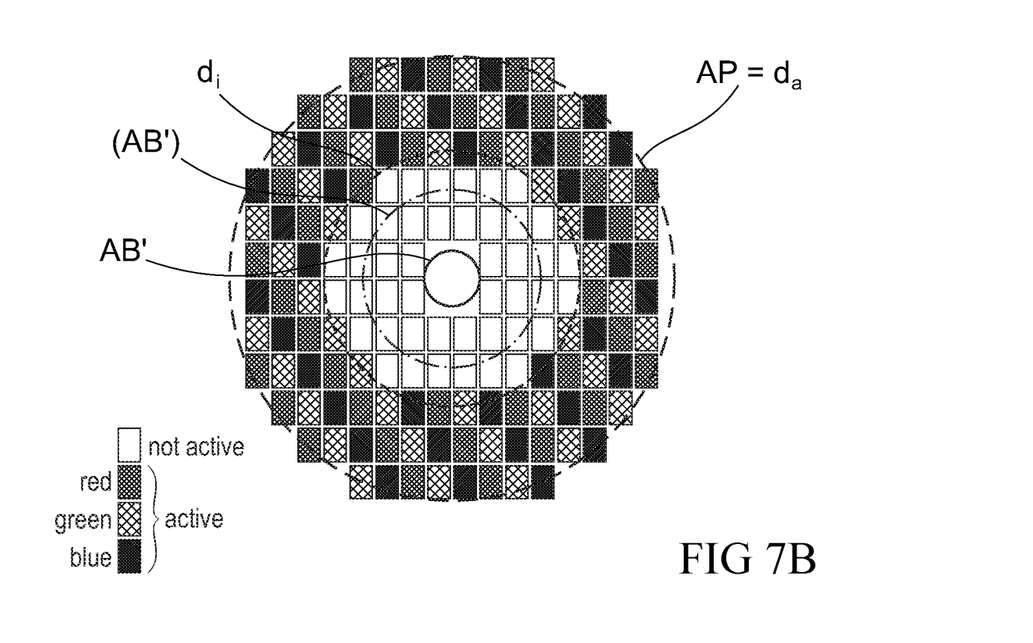
FIG. 7B shows a second embodiment example of an illumination unit as an adaptive, structurable arrangement of light sources.
Figure 7C:
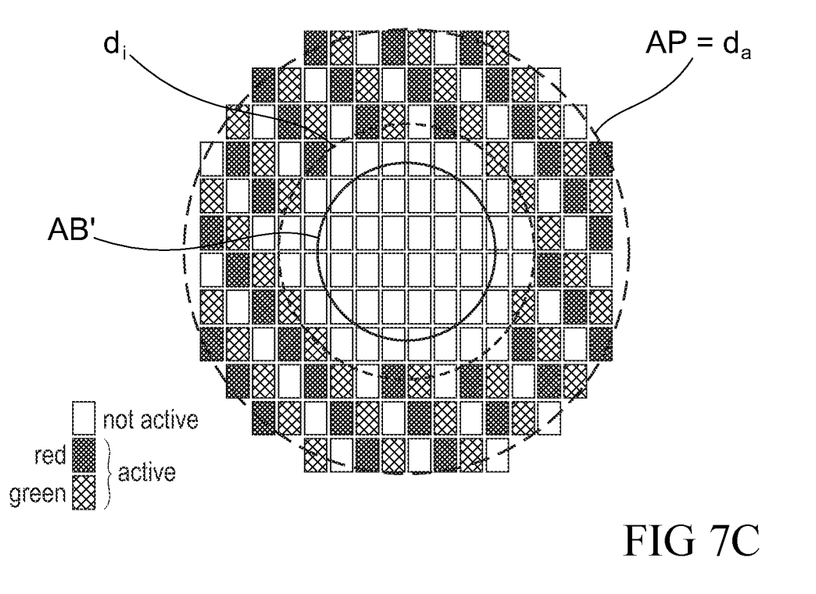
FIG. 7C shows a third embodiment example of an illumination unit as an adaptive, structurable arrangement of light sources.
Figure 7D:
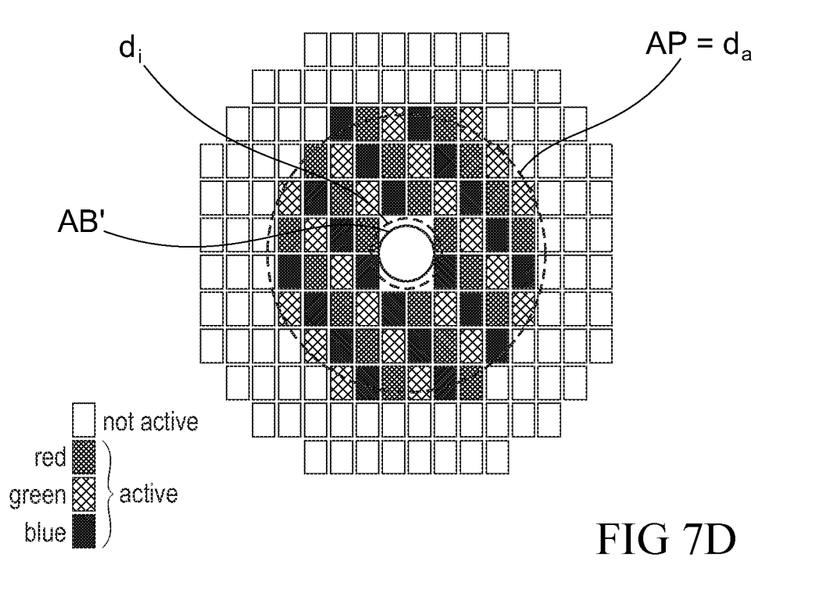
FIG. 7D shows a fourth embodiment example of an illumination unit as an adaptive, structurable arrangement of light sources, and 7E shows a fifth embodiment example of an illumination unit as an adaptive, structurable arrangement of light sources.

FIGS. 7B and 7D show comparative views of pupils AP with a large and a small opening, respectively. The illumination structure, formed by activated LEDs, which are represented by different types of hatching, and the aperture stop AB, which is embodied, for example, as an iris with a variable diameter, are adapted such that an optimal luminous flux enters the eye A or an optimal diameter of the aperture stop AB is set for high image resolution. Also, when changing the external diameter $d_a$ of the illumination structure and accordingly adapting the internal diameter $d_i$, the area of the illumination structure can be kept constant so as to keep the incident luminous flux stable by compensation. In this case, the external diameter $d_a$ is optimally adapted to the opening of the pupil AP or of the iris, respectively.

FIGS. 7A and 7B show, in comparative views, that the internal diameter $d_i$ is opened wide while the opening of the pupil AP remains the same. This produces either a large radiation-free space between the illumination beam, internally limited by the internal diameter $d_i$, and the observation beam, limited by the image AB' (continuous line in FIG. 7B) of the small aperture stop AB, thus achieving a reduction of scattered light, especially in older patients. Or, for a large aperture stop AB (AB' as a dashed/dotted line in FIG. 7B), the imaging properties are comparatively improved and more light is provided to the digital image sensor 2.

Figure 7E:
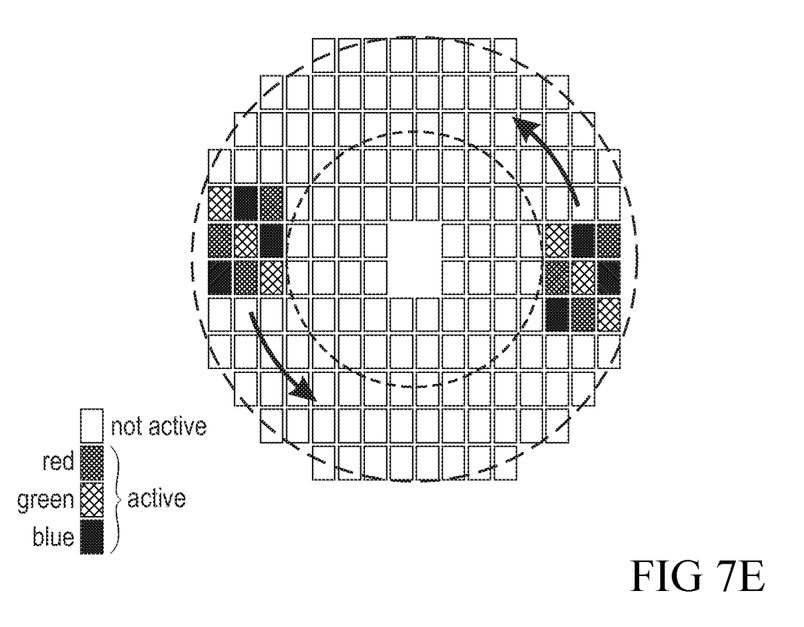

In conventional illumination units, there is the frequent problem that the illumination beam path is cut off by drooping eyelids, long eyelashes or a slanted eye shape, thereby allowing less light into the eye A, which causes the image quality to deteriorate and may even result in the examination being aborted. By activating and deactivating LEDs, as shown in FIG. 7E, an illumination structure can be created, which evades cutoffs. Also, in older patients there is the frequent problem of cataracts considerably affecting image quality. Even in this case, by changing the location of the illumination structure, as shown by way of example in FIG. 7D, the illumination beam path can be made to bypass more heavily clouded areas of the eye lens. For this purpose, for example by controlling such an illumination structure in a rotary manner, the position of the illumination beam path can be optimized.

Advantageously, also in order to remove irritating vascular reflections on the ocular fundus or to allow the higher-contrast representation of vessels and other objects on the ocular fundus, the beam direction of illumination beams incident on the ocular fundus may be changed by differentiated control of the LEDs.

FIG. 7C shows, by way of example, that only the green and red LEDs are activated which generate the measuring light in the exemplary embodiment.

Another advantageous alternative embodiment of a digital image sensor 2 is a monochromatic image sensor recording color images. For this purpose, three monochromatic images are respectively combined in quick succession, each of said three monochromatic images being assigned a different LED color for illumination. The three images are each subsequently combined into one color image (image with three assigned color channels).

The adaptive control unit 4 is connected to a data and image processing unit 5, which is in turn connected to the digital image sensor 2. The frequency of the flicker light (change between bright and dark) is controlled by a synchronization signal which, in this exemplary embodiment, is generated by the digital image sensor 2 and is transmitted to the control unit 4, and is synchronized in order to synchronize all signals formed during the process steps with the image sequence recorded by the digital image sensor 2. For the invention, it does not matter whether the synchronization signal is given by the digital image sensor 2 or by the data and image processing unit 5 and controls the recording of the images of the image sequence.

The digital image sensor 2 records images of the fundus F at an imaging frequency of preferably 25 Hz, which preferably results in a flicker frequency of 12.5 Hz. However, according to the invention, any other imaging frequency synchronized with a flicker frequency may be used for the device and the method. In this case, a variable imaging and flicker frequency may also be used to address different questions.

The data and image processing unit 5 selects the papilla P, the image of the macula stop MB, optionally with the web ST, as well as arterial and venous large vessels of the retina in each image, records the movement coordinates of the fundus F following the fixation mark FM and uses them for movement correction of the images of the image sequence or of the measurement data and signals, respectively.

Furthermore, a unit for generating diameter signals 6 is provided, which determines the vessel diameters in the selected vascular segments and generates, for each vascular segment, as a function of time and location, diameter signals $D(t,x,y)$ for an image sequence and transmits these signals to the signal analysis unit 7. There, the signals of the vascular segments are used to form averaged diameter signals $D(t, x,y)$ for entire vascular sections by averaging after combining several vascular segments, said signals being graphically displayed and output to the examiner for presentation. In the signal analysis unit 7, typical parameters of the vessels, describing the endothelial function, such as, for example, the maximum flicker dilation $FD_{max}$ in the stimulation phase SP, are also computed and output via the result and presentation unit 8 and the input and output unit 9. The result and presentation unit 8 additionally serves to generate mapping images.

The method according to the invention will be explained below with reference to an exemplary embodiment.

Step 0:

An examination program menu for different examinations relating to different medical questions is presented to the examiner. The selection of examination parameters serves to adjust the arrangement of the at least one macula stop MB, the parameters of the fixation light, provided the fixation mark FM is formed by a self-luminous mark, the parameters of the measuring light and the parameters of the flicker light.

The examiner can choose between adjusting
0-1: freely selected parameters (free parameter selection),
0-2: comparative parameters (comparative mode), and
0-3: repetition parameters (repeat mode),
as described in the following process steps:

Step 0-1: Free parameter selection

For questions in research, free parameter selection is often useful. The following parameters are preferably presented to the examiner for automatic pre-selection, and after selection the set of parameters is stored as a new program for comparative and repeat examinations under a name to be assigned by the examiner.

Step 0-1-1: Adjustment of the Type and Location of the Macula Stop MB as Well as of the Fixation Point (Fixation Parameters)

The type and location of the one or more macula stops MB and, optionally, of the web ST are displayed to the examiner as an image for manual adjustment or preset automatically.

The examiner then selects the type of fixation by setting the following fixation parameters for the fixation mark FM:
  spectral determination of the geometric fixation structure (cross, point, ring . . . )
  determination of the fixation color
  determination of the fixation intensity
  determination of the temporal changes in fixation intensity (e.g. flash frequency)
  or use of an opening in the macula stop MB as a fixation mark FM, which is illuminated by the flicker and measuring light Step 0-1-2: Adjustment of the Measuring Light (Measuring Light Parameters)
  determination of the spectral range (preferably green); for special issues, measuring light from different spectral ranges may also be used
  determination of the intensity (manually or automatically re-adjustable, controlled by image brightness)
  determination of the time response during the stimulation phase SP In this manner, the flicker light for stimulation and the measuring light may be synchronized with each other, independently, for the medical issue.

Step 0-1-3: Adjustment of the Flicker Light Parameters
Adjustment to luminance flicker or color flicker For luminance flicker, the defined spectral range of the flicker light is modulated only in accordance with the other flicker parameters. In the case of color flicker, the flicker light only changes the spectral range with the flicker frequency, which means mutual switching of the different-color LEDs.
  the adjustment of the spectral ranges of the color LEDs is performed in accordance with the flicker type, e. g. in the case of color flicker, the flicker light is set to change from a blue LED to a green LED
  adjustment of the modulation of the flicker light (modulation parameters)

In the present example, the examiner may define the form of stimulation for each half-period of the flicker light with the following parameters:
  intensity maximum
  intensity minimum
  modulation depth
  intensity increase
  intensity decrease
  duration of the intensity maximum
  wave-shaped or step-shaped modulation Step 0-1-4: Adjustment of the Examination Phases (Phase Parameters)
  this involves adjustment of the duration of the examination phases: baseline phase BP, stimulation phase SP, and posterior phase NP
  in the case of an adaptive stimulation phase SP, adjustment is performed:
    of a minimum duration of the stimulation phase SP
    of a maximum duration of the stimulation phase SP
    and of the abort parameters for the stimulation period
  Step-0-1-5:
  All freely selected parameters are combined in a set of parameters and stored with a special examination name and presented upon renewed selection of the examination menu Step 0-2: Comparative Mode (Ensures the Same Examination Conditions for Different Eyes a for the Same Medical Question)

The desired examination program for the medical question is selected from the examination menu and the respective set of parameters for the selected examination program is loaded. The LEDs of the device are controlled accordingly via provided control algorithms, thereby adjusting the measuring light and the flicker light to the selected examination program in a variable and adaptive manner.

Step 0-3: Repeat Mode (Ensures the Same Examination Conditions in Follow-Up Sessions for the Same Eye A) with Reference Measurement Locations The eye A already examined previously is selected from the patient-related database, with both the data sets stored for the selected vessels and the set of parameters of the examination performed being preset.

During the adjustment of the device to the eye A, the movement correction ensures an exact match of the recorded areas of the fundus F between the sessions.

After adjustment of all parameters, the examination procedure begins.

Step 1:
The patient's head is held in place by a head and chin rest. The patient is asked to look at the fixation mark FM on the dark macula stop MB.

Step 2:
The device is adjusted to the eye A to be examined, by means of a cross table so as to result in a low-scatter and non-reflecting image of the fundus F.

Step 3:
The image of the fundus F and the macula stop MB are focused, and by rotating the web ST, the web ST of the macula stop MB is positioned such that it covers the papilla P of the eye A to be examined Step 4:
The measuring process of the examination is started as soon as recording of an image sequence begins during the baseline phase BP, wherein only measuring light, and no flicker light, is used.

Step 5:
By algorithms
  5.1: the position of the web ST in the light field LF is detected and, thus, the examined eye A (right or left) is automatically identified.
  5.2: the central residual reflections of the ophthalmoscope lens OL are detected centrally and blocked out electronically.
  5.3: the image of the first field stop FB of the illumination beam path 1.1 of the fundus camera 1 is identified on the fundus F.

5.4: the scattered light distribution outside the light field LF and in the area not blocked out by the macula stop MB is computed and subtracted from the recorded image of the fundus F.

5.5: the images are movement-corrected with respect to the eye movements.

5.6: the papilla P is selected and blocked out, e.g. for applications in static vessel analysis.

5.7: the large arterial and venous vessels of the uncovered retina are selected and stored.

Step 6:

Algorithms for diameter measurement are used to determine vessel diameters along the selected vessels, one vascular segment after another, stored in location-corrected form and assigned to the synchronization signal and, consequently, to the individual images of the image sequence. Based on this data, diameter signals D(t,x,y) are formed for each vascular segment.

Step 7:

First, the baseline phase BP is started with a baseline time. This is automatically followed by the stimulation phase SP with the stimulation time (flicker period) and the set of parameters provided for the flicker light.

Step 8:

During the stimulation phase SP, all vascular signals are normalized to their respective average baseline value (determined on the basis of the baseline phase BP) on a percentage basis. The flicker-induced changes in all vascular signals during the stimulation phase SP are averaged separately for arteries $A_V$ and veins $V_V$ and evaluated with respect to their scatter and dilation. According to the invention, when selecting the adaptive stimulation phase SP, the stimulation time is made dependent on the examination result. If the increase in flicker dilation and the scatter of the average flicker dilation is below a predetermined threshold value after 20 s, the stimulation phase SP is terminated.

The average flicker dilation of all arterial and venous vascular segments is output separately.

Step 9:

After terminating the stimulation phase SP, the posterior phase NP of the examination begins, the flicker light is deactivated and the continuous measurements are continued until the posterior phase NP is terminated after the preset time. The posterior phase NP may also be configured to be adaptive by terminating it when the average signal changes and the scatter of the signal values are below a threshold value or another criterion is used for termination. The stimulation phase SP and the posterior phase NP may be repeated alternately several times, preferably three times, for averaging the signals.

Step 10:

Further average parameters, such as e.g. average parameters of vasomotion in the baseline or the constriction following the decrease in dilation, are formed from the diameter signals D(t,x,y) over all vascular segments, separately for arteries $A_V$ and veins $V_V$.

Step 11:

An average arterial and an average venous vascular signal D=f(t) are formed over all vascular segments and output as an examination result together with the average parameters in an examination report.

Step 12:

For each parameter, in particular for the maximum flicker dilation $FD_{max}$ of the arterial and venous vascular segments, the values have colors assigned to them, which are then represented as functional imaging in the image of the fundus F, superimposed in the correct position. Red segments identify a missing maximum flicker dilation $FD_{max}$ and green segments identify a healthy maximum flicker dilation $FD_{max}$.

It does not matter for the method according to the invention if the adjustment and certain process steps of the evaluation are performed manually or automatically.

An advantageous embodiment of the device and method according to the invention is the optoelectronic realization of the macula stop MB and further stops in the plane conjugated to the fundus F in the illumination beam path 1.1, e.g. by a transmission display whose pixels are independently electronically adjustable in their transmission. During the method of the invention, the display is then controlled by software in accordance with the individual process steps, analogous to the adjustment of a mechanical macula stop MB.

LIST OF REFERENCE NUMERALS

NVK neurovascular coupling
RVA Retinal Vessel Analyzer from Imedos
DVA Dynamic Vessel Analyzer from Imedos
D(t,x,y) diameter signal as a function of time and location x, y on the fundus F
$FD_{max}$ maximum flicker dilation
BP baseline phase (recording of the signals without stimulation)
SP stimulation phase (recording of the signals during stimulation)
NP posterior phase (recording of the signals after stimulation)
1 fundus camera
1.1 illumination beam path
1.2 observation beam path
2 digital image sensor
2.1 reception surface
2.2 differential area
3 illumination unit
4 control unit
5 data and image processing unit
6 unit for generating diameter signals
7 signal analysis unit
8 result and presentation unit
9 input and output unit
A eye
F fundus
M macula
P papilla
V foveola
$V_V$ vein
$A_V$ artery
AP pupil
MB macula stop
FMP area center of the macula stop
FM fixation mark
ST web
FB field stop
KL collimator lens
FL field lens
OL ophthalmoscope lens
CO objective lens
LB pinhole stop
AB aperture stop in the observation beam path 1.2
AB' image of the aperture stop AB in the pupil AP
F''' plane conjugated to the fundus F in the illumination beam path 1.1

F', F'' planes conjugated to the fundus F in the observation beam path 1.2
AP'' plane conjugated to the pupil AP in the illumination beam path 1.1
AP' plane conjugated to the pupil AP in the observation beam path 1.2
LF light field
$d_i$ internal diameter of an illumination structure
$d_a$ external diameter of an illumination structure

What is claimed is:

1. A method for examining a retinal vascular endothelial function of vessels of a retina at a fundus (F) of an eye (A), the method comprising:

adjusting a fundus camera to the eye (A);
generating measuring light for illuminating the vessels of the retina at the fundus (F) and generating illuminating flicker light for stimulation of the vessels of the retina at the fundus (F) during a stimulation phase (SP);
generating an image sequence of images of an area of the fundus (F) during a baseline phase (BP), at least one stimulation phase (SP) and at least one posterior phase (NP);
measuring vessel diameters of selected vascular segments of the vessels of the retina in the images of the image sequence as a function of location and time;
performing movement correction for the vascular segments, wherein each vascular segment is assigned to a location on the fundus (F) in a movement-corrected manner;
forming diameter signals (D(t,x,y)) representing the measured vessel diameters as a function of the time and location of each selected vascular segment; and
deriving as vascular parameters the maximum flicker dilation from the diameter signals (D(t,x,y)) of each selected vascular segment, each of said vascular parameters describing the endothelial function of a respectively selected vascular segment;
wherein illuminating and stimulating a macula (M) at the fundus (F) is prevented by projecting a sharp image of one macula stop (MB) with a fixation mark (FM) attached to it onto the fundus (F), and aligning the eye (A) with said one macula stop (MB) by fixation on the fixation mark (FM) of said one macula stop (MB) such that the macula (M) is covered by an image of said one macula stop (MB).

2. The method according to claim 1, further comprising sequentially recording image sequences of images of different selected areas of the fundus (F) at any one time after only one macula stop (MB) imaged onto the fundus (F) has been shifted to a different location so that its image on the fundus (F) has been shifted and the eye (A), fixating on the fixation mark (FM), has followed.

3. The method according to claim 2, further comprising storing location parameters of the locations of the macula stop (MB), the location parameters being retrievable and adjustable for repeat and follow-up measurements.

4. The method according to claim 1, alternatively comprising recording image sequences of different predetermined areas of the fundus (F) while imaging four macula stops (MB) diagonally arranged opposite each other onto the fundus (F), and sequentially fixating the eye (A) on a different fixation mark (FM) in each case.

5. The method according to claim 1, further comprising independently adjusting durations of the baseline phase (BP), the stimulation phase (SP), the posterior phase (NP), and the parameters of the measuring light and of the flicker light and storing them in a manner assigned to a patient and to an examination program in order to be retrievable and adjustable again as a set of parameters for repeat and comparative examinations.

6. The method according to claim 1, further comprising determining a maximum flicker dilation (FDmax) as one of the derived vascular parameters, the maximum flicker dilation (FDmax) being an output in a measurement report together with a graphical representation of averaged diameter signals (D(t,x,y)), the averaged diameter signals (D(t,x,y)) each being respectively generated for the selected arterial and venous vascular segments on the basis of the diameter signals (D(t,x,y)).

7. The method according to claim 1, further comprising assigning in a color-coded manner the maximum flicker dilation (FDmax) to the respective vascular segment in a mapping image for functional imaging of the endothelial function, wherein a missing vasodilation or a vasodilation below a predetermined threshold value is marked in red and a vasodilation above a threshold value corresponding to a healthy vascular function is marked in green on the associated vascular segment, and wherein the mapping image is serves as an output of a graphical examination result.

\* \* \* \* \*